(12) United States Patent
Griffin et al.

(10) Patent No.: US 6,677,345 B1
(45) Date of Patent: Jan. 13, 2004

(54) CYCLIN DEPENDENT KINASE INHIBITORS

(75) Inventors: Roger J Griffin, Northumberland (GB); Alan H Calvert, Tyne & Wear (GB); Nicola J Curtin, Tyne & Wear (GB); David R Newell, Northumberland (GB); Bernard T Golding, Newcastle Upon Tyne (GB); Jane A Endicott, Oxford (GB); Martin E M Noble, Oxford (GB); Francis T Boyle, Congleton (GB); Philip J Jewsbury, Cheshire (GB)

(73) Assignee: Cancer Research Campaign Technology Limited, London (GB)

( * ) Notice: Subject to any disclaimer, the term of this patent is extended or adjusted under 35 U.S.C. 154(b) by 0 days.

(21) Appl. No.: 09/671,676

(22) Filed: Sep. 28, 2000

Related U.S. Application Data (63) Continuation of application No. PCT/GB99/00830, filed on Mar. 29, 1999.

(51) Int. Cl.[7] ................. A61K 31/505; A61P 35/00; C07H 19/167; C07D 487/00; C07D 239/02
(52) U.S. Cl. ................. 514/274; 514/45; 536/27.8; 536/27.81; 544/262; 544/309; 544/310; 544/313
(58) Field of Search ................. 514/45, 274; 536/27.8, 536/27.81; 544/262, 309, 310, 313

(56) References Cited

U.S. PATENT DOCUMENTS

| | | | | |
|---|---|---|---|---|
| 5,525,606 A | * | 6/1996 | Moschel et al. ............. | 514/262 |
| 5,929,046 A | * | 7/1999 | MxMurry et al. ............. | 514/45 |

* cited by examiner

Primary Examiner—Richard L. Raymond
Assistant Examiner—Tamthom N. Truong
(74) Attorney, Agent, or Firm—Pillsbury Winthop LLP (57) ABSTRACT

A range is disclosed of pyrimidine derivatives (I) which can act as inhibitors of cyclin dependent kinases (CDK's) and which thereby can provide useful therapeutic compounds for use in treatment of tumours or other cell proliferation disorders. The compounds of this invention bind to CDK molecules in a manner that appears to differ from that of known CDK inhibitors such as olomoucine and roscovitine. In formula (I), X is O, S or $CHR_x$ where $R_x$ is H or $C_{1-4}$ alkyl; D is H or $NZ_1Z_2$ where $Z_1$ and $Z_2$ are each independently H, $C_{1-4}$ alkyl, $C_{1-4}$ hydroxyalkyl, optionally substituted aryl or optionally substituted aralkyl; A is selected from H, $C_{1-4}$ alkyl, $C_{1-4}$ alkoxy, hydroxy, $CH_2(CH_2)_nOH$ (n=1–4), and $NR_{a1}R_{a2}$ where $R_{a1}$ and $R_{a2}$ are each independently H or $C_{1-4}$ alkyl; Y is or includes an optionally substituted 4- to 8-membered carbocyclic or heterocyclic ring; D' is H or $NZ_3Z_4$ where $Z_3$ and $Z_4$ are each independently H, $C_{1-4}$ alkyl, $C_{1-4}$ hydroxyalkyl, optionally substituted aryl or optionally-substituted aralkyl; E is selected from NO, $NO_2$, N=N—Ar where Ar is an optionally substituted aryl or optionally substituted aralkyl, $NR_{e1}R_{e2}$ or $Nr_{e1}Nr_{e2}R_{e3}$ ($R_{e1}$, $R_{e2}$ and $R_{e3}$ each being independently H, $C_{1-4}$ alkyl, $C_{1-4}$ hydroxyalkyl, an optionally substituted aryl or an optionally substituted aralkyl), $C(R_e)$=U ($R_e$ being hydrogen, $C_{1-4}$ alkyl or substituted alkyl, e.g. hydroxyalkyl, or an unsubstituted or substituted aryl or aralkyl, e.g. benzyl, and U being selected from O, $Nr_e'$, $NOR_e'$ and $N—NR_e'R_e''$ where $R_e'$ and $R_e''$ are each independently H, $C_{1-4}$ alkyl or $CONH_2$), T, $CH_2T$, $CHT_2$ and $CT_3$, where T is a halide I, Br, Cl or F.

(I)

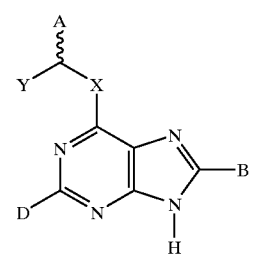

28 Claims, 2 Drawing Sheets

CYCLIN DEPENDENT KINASE INHIBITORS

This is a continuation of PCT/GB99/00830 filed on Mar. 29, 1999.

FIELD OF THE INVENTION

The present invention relates to certain compounds, especially pyrimidine derivatives, which show activity in biological systems as cyclin dependent kinase (CDK) inhibitors and which are accordingly of interest as potentially useful therapeutic agents that may be incorporated in pharmaceutical compositions or formulations for use in controlling or inhibiting cell growth or proliferation in mammals, for example in connection with antitumour or cancer treatment.

BACKGROUND

Cyclin dependent kinases (CDK's) are a family of enzymes which form complexes with other activating proteins known as cyclins to provide key regulatory factors that are involved in the control of growth and division in animal cells. More particularly, the progression of animal cells through the cell division cycle (G1, S, G2 and M phases) is regulated by the sequential formation, activation and subsequent inactivation of a series of CDK/cyclin dimer complexes which control passage past cell cycle checkpoints and transitions between successive phases of the cell cycle, with the CDK's acting as catalytic sub-units of the complexes.

There are in fact a number of different cyclin proteins which, like the different CDK's, form a somewhat loosely related family of CDK-activating proteins; different CDK/cyclin complexes function at different stages of the cell cycle with sequential increase and decrease in cyclin expression during the cell cycle and cyclin degradation during M phase usually being an important factor in determining orderly cell cycle progression. Thus, progression through G1 to S phase in mammalian cells is believed to be regulated primarily by cyclin dependent kinases CDK2, CDK3 and CDK4 (and possibly also CDK6 in some cells) in association with at least cyclins D and E, the complexes of CDK2 and CDK4 (and possibly CDK6) with D type cyclins in particular playing an important role in controlling progression through the G1 restriction point whilst the CDK2/cyclin E complexes are essential for bringing about the transition from G1 into S phase. Once S phase is entered it is believed that further progression and entry into G2 then requires activated complexes of CDK2 with another cyclin which is designated cyclin A, i.e. complexes CDK2/cyclin A. Finally, for the transition from G2 phase to M phase and initiation of mitosis, activated complexes of the cyclin dependent kinase designated CDK1 (also known as Cdc2) with a cyclin designated cyclin B (and also complexes of CDK1 with cyclin A) are required.

In general, control of the cell cycle and activity of CDK's involves a series of stimulatory and inhibitory phosphorylation and dephosphorylation reactions, and in exercising their regulatory functions the CDK/cyclin complexes when activated use ATP as a substrate to phosphorylate a variety of other substrate cell proteins, usually on serine and threonine groups thereof. Control of the cell cycle may also involve inhibitors of CDK/cyclin complexes which block the catalytic function of these enzymes so as to lead to arrest of the cell cycle. Certain natural inhibitors, such as for example the inhibitory proteins known as p16 and p21, can block cell cycle progression by binding selectively to CDK/cyclin complexes to inactivate the latter.

Control by inhibitors of CDK function may therefore provide a further mechanism for controlling cell cycle progression, and this has led to proposals for using CDK inhibitors as antiproliferative therapeutic agents, in antitumour therapy for example, for targeting abnormally proliferating cells and bringing about an arrest in cell cycle progression. This has seemed to be especially appropriate since it is known that severe disorders or irregularities in cell cycle progression frequently occur in human tumour cells, often accompanied by over-expression of CDK's and other proteins associated therewith. Also, compared to established cytotoxic antitumour drugs, the use of inhibitors of cell proliferation acting through CDK's would have the advantage of avoiding a direct interaction with DNA, thereby giving a reduced risk of secondary tumour development.

The potential therapeutic applications and other possible uses have accordingly led to a search for further chemical inhibitors of CDK's, especially selective inhibitors that may be suitable for pharmaceutical use. Inhibitory activity and selectivity of selected CDK/cyclin complexes is generally assayed by measuring the kinase activity in phosphorylating the protein histone H1 (one of the major protein constituents of chromatin which generally provides a good CDK substrate) in the presence of the suspected inhibitor under test. A number of compounds having potentially useful CDK inhibitory properties that have been identified in this way are described in a review article, of which the content is incorporated herein by reference, entitled "Chemical inhibitors of cyclin-dependent kinases" by Laurent Meijer published in *Cell Biology* (Vol. 6), October 1996. Among the compounds referred to in the above-mentioned article is a potent CDK1 and CDK2 inhibiting adenine derivative 2-(2-hydroxyethylamino)-6-benzylamino-9-methyl-purine, named "olomoucine", and also a close analogue incorporating modifications at positions 2, 6 and 9, namely, 6-(benzylamino)-2(R)-[{1-(hydroxymethyl)propyl}amino]-9-isopropylpurine. This latter compound is named "roscovitine" and is even more potent than olomoucine as a CDK inhibitor. The strong but selective CDK inhibitory properties of olomoucine were first described in a paper by J. Vesely et al entitled "Inhibition of cyclin-dependent kinases by purine analogues", *Eur. J. Biochem.* 224, 771–786 (1994), and further studies on CDK inhibitory properties of a range of purine compounds in the form of adenine derivatives, including olomoucine and roscovitine, are reported and discussed in a paper by L. Havlicek et al entitled "Cytokinin-Derived Cyclin-Dependent Kinase Inhibitors: Synthesis and cdc2 Inhibitory Activity of Olomoucine and Related Compounds" *J. Med. Chem.* (1997) 40, 408–412. Again, the content of these publications is to be regarded as being incorporated herein by reference.

The inhibitory activity of both olomoucine and roscovitine has been shown to result from these compounds acting as competitive inhibitors for ATP binding. It may be noted that olomoucine at least is reported as having a total lack of inhibitory activity in relation to many common kinases other than CDK's. Selectivity is further manifest by the fact that both olomoucine and roscovitine inhibit activity of CDK1, CDK2 and CDK5, but neither has been found to be active against CDK4 or CDK6.

Olomoucine in particular has been regarded as providing a lead compound for helping to identify and design further purine based CDK inhibitors, and based on structure/activity studies it was suggested in the above-mentioned paper of Vesely et al that N9 substitution by a hydrophobic residue such as methyl, 2-hydroxyethyl or isopropyl was important, e.g. to provide a direct hydrophobic interaction with the CDK, and that a side chain at C2 appeared to be essential. Similarly, in the paper of Havlicek et al, apart from observing that for purine compounds to have CDK inhibitory activity the 1 and 7 positions, and possibly the 3 position, of the purine ring must remain free to permit hydrogen bonding, it was also stated that a polar side chain at position 2 appears to be essential and that N9 substitution by a hydrophobic residue is also probably important for positive binding. Positions 2, 6 and 9 in the purine ring were identified as being the positions which control to CDK1.

In the review article of Meijer, it is also mentioned that as a result of crystallization of CDK-inhibitor complexes, and in particular co-crystallization studies with CDK2, it has been found that inhibitors such as olomoucine and roscovitine localize in the ATP binding pocket which is located in the cleft between the small and large lobes of the CDK protein molecule, and that specificity was probably provided by portions of the inhibitor molecules interacting with the kinases outside the ATP binding sites.

SUMMARY OF THE INVENTION

The present invention has developed from an observation made in the course of testing various guanine derivatives for activity as inhibitors of the DNA repair protein $O^6$-methylguanine DNA-methyltransferase (MGMT) when it was found unexpectedly that although the compound $O^6$-cyclohexylmethylguanine had very little activity as a MGMT inhibitor, it was nonetheless cytotoxic and showed very high inhibitory activity, comparable to that of olomoucine, against CDK1(cdc2)/cyclin B complexes. This was particularly surprising against the background discussed above in relation to olomoucine given that this guanine compound has no substituents at either the 2-$NH_2$ position or the 9 position in the purine ring and that the replacement of the 6-NH by 6-O made the compound less like ATP with which olomoucine at least is believed to compete for binding sites.

Subsequently, other guanine derivatives have been identified, more closely related to $O^6$-cyclohexylmethylguanine than to compounds such as olomoucine and roscovitine, which show significant CDK inhibitory activity, and crystallographic studies have revealed that complexes of CDK2 (homologous with CDK1, at least in respect of the catalytic binding site) with guanine derivatives such as $O^6$-cyclohexylmethylguanine and $O^6$-cyclohex-1-enylmethylguanine bind together in a different manner from complexes of CDK2 with olomoucine.

BRIEF DESCRIPTION OF DRAWINGS

This is illustrated in the accompanying drawings in which.

Figure 2:
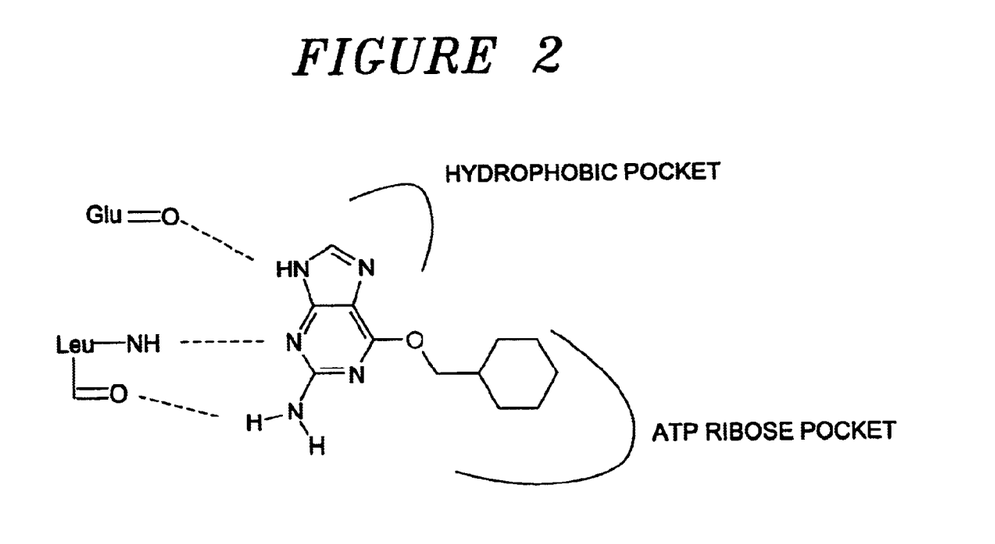
FIG. 2 is a similar diagram indicating the manner in which the compound $O^6$-cyclohexylmethylguanine has been found to bind to CDK2.
Figure 3:
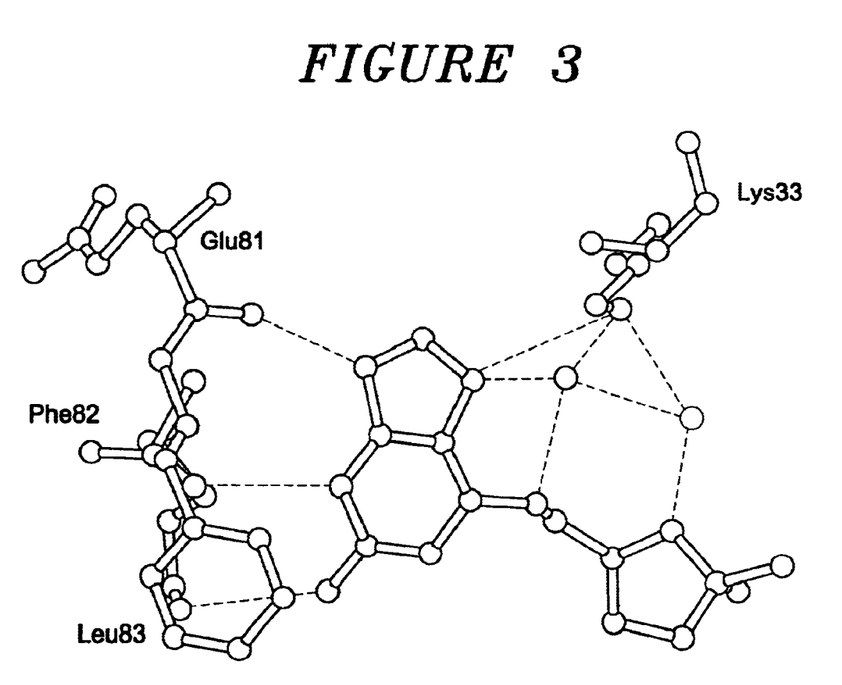
FIG. 3 is a diagram representing a crystal structure showing the manner in which the R enantiomeric form of the compound $O^6$-(2,2-dimethyl-1,3-dioxolane-4-methoxy)-guanine has been found to bind to CDK2.

Whereas with olomoucine it is the polar side chain on N2 of the purine ring that seats within the ATP ribose binding pocket of the CDK2 protein, and the N9 methyl substituent engages a separate hydrophobic specificity pocket, with N7 and 6-NH being involved in hydrogen bonding to the protein, in the binding mode illustrated in FIG. 2 it is the cycloalkyl ring of the substituent at the 6-position that seats in the ATP ribose binding pocket while hydrogen bond links are formed to N9, N3 and 2-NH. In other words, the orientation as compared with the binding of olomoucine is completely reversed. A similar situation obtains with the binding mode illustrated in FIG. 3 where the involvement of some water molecules is also indicated.

Figure 1:
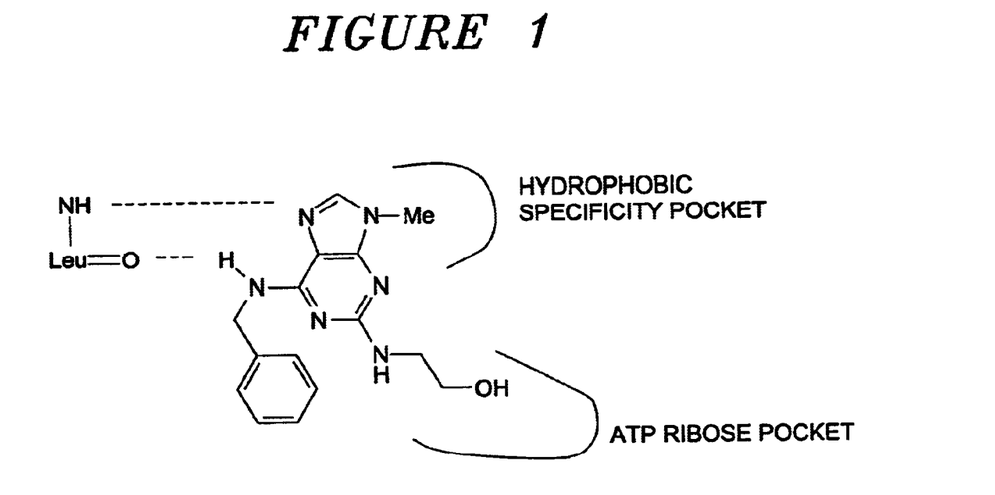
FIG. 1 is a diagram indicating the manner in which olomoucine binds to CDK2.

It will accordingly be clear that conclusions reached in respect of structure/activity relationships in the adenine series of compounds exemplified by olomoucine and roscovitine are likely no longer to be valid for all purine derivatives, especially guanine derivatives, and as disclosed in our co-pending International Patent Application No. PCT/GB98/02025 a range of other purine compounds has been identified which have inhibitory activity in respect of at least some CDK's and which are believed to bind in the manner shown in FIG. 2 (or FIG. 3) rather than in the manner shown in FIG. 1.

It has now been found that there are also a number of single ring nitrogen-containing heterocyclic compounds, especially pyrimidine compounds, which when provided with suitable substituents can act like or mimic the above-mentioned purine compounds and exhibit inhibiting activity in respect of at least some CDK proteins. Like the purine compounds, for CDK inhibiting activity these pyrimidine compounds will be linked in the 4-position through a side chain to an optionally substituted 4- to 8-membered carbocyclic or heterocyclic ring which, it is believed, will seat in the ATP ribose binding pocket of the CDK protein. Also, there will usually be an amino or partially-substituted amino group at the 6-position which will interact with a hydrophobic specificity pocket of the CDK protein in a manner analogous to that shown in FIG. 2 or FIG. 3 for the binding of a CDK inhibiting purine. Preferably, there will also be an amino or substituted amino group at position 2.

More particularly, in one aspect the present invention provides pharmaceutical compositions for treatment of cell proliferation disorders in mammals, for example tumours, said compositions containing as the active ingredient a CDK-inhibiting pyrimidine compound having the structural formula I below:

I in which, in preferred embodiments,

X is O, S or $CHR_x$ where $R_x$ is H or $C_{1-4}$ alkyl;

D is H or $NZ_1Z_2$ where $Z_1$ and $Z_2$ are each independently H, $C_{1-4}$ alkyl, $C_{1-4}$ hydroxyalkyl, optionally substituted aryl or optionally-substituted aralkyl;

A is selected from H, $C_{1-4}$ alkyl, $C_{1-4}$ alkoxy, hydroxy, $CH_2(CH_2)_n OH$ (n=1–4), and $NR_{a1}R_{a2}$ where $R_{a1}$ and $R_{a2}$ are each independently H or $C_{1-4}$ alkyl;

Y is or includes an optionally substituted 4- to 8-membered carbocyclic or heterocyclic ring;

D' is H or $NZ_3Z_4$ where $Z_3$ and $Z_4$ are each independently H, $C_{1-4}$ alkyl, $C_{1-4}$ hydroxyalkyl, optionally substituted aryl or optionally-substituted aralkyl;

E is selected from H, NO, $NO_2$, N=N—Ar where Ar is an optionally substituted aryl or optionally substituted aralkyl, $NR_{e1}R_{e2}$ or $NR_{e1}NR_{e2}R_{e3}$ ($R_{e1}$, $R_{e2}$ and $R_{e3}$ each being independently H, $C_{1-4}$ alkyl, $C_{1-4}$ hydroxyalkyl, an optionally substituted aryl or an optionally substituted aralkyl), $C(R_e)$=U ($R_e$ being hydrogen, $C_{1-4}$ alkyl or substituted alkyl, e.g. hydroxyalkyl, or an unsubstituted or substituted aryl or aralkyl, e.g. benzyl, and U being selected from O, $NR_e'$, $NOR_e'$ and N—$NR_e'R_e''$ where $R_e'$ and $R_e'$ are each independently H, $C_{1-4}$ alkyl or $CONH_2$), T, $CH_2T$, $CHT_2$ and $CT_3$, where T is a halide I, Br, Cl or F.

Certain of the compounds within the scope of the above definition are already known per se, but have not been previously known in a capacity as CDK inhibitors. Some of these compounds are believed to be new chemical entities. Moreover, in some cases the CDK inhibitory activity has been found to have a selectivity towards different CDK's which is notably different from that of olomoucine. Thus, the present invention has in effect identified a further class of CDK inhibitors and has considerably enlarged the range of compounds available for use as CDK inhibitors.

So long as it is able to fit or seat in the ATP ribose binding pocket of a CDK protein and permit binding in the general manner depicted in FIG. 2 rather than FIG. 1, there is a wide range of substituents likely to be suitable for Y. In some cases it may be helpful for Y to comprise a ring structure that includes polar hydroxyl substituents or the like.

In most embodiments Y will be a cycloalkane or cycloalkene ring, preferably a 5- or 6-membered ring having up to two double bonds. One or two carbon atoms in the ring may be replaced, however, by hetero atoms or groups, particularly O, S, NR' (where R' is H or $C_{1-4}$ alkyl) or, in a cycloalkene ring, —N=. Where the ring is substituted the substituent or each substituent (at any position) will preferably be selected from H, $C_{1-4}$ alkyl, OH, $C_{1-4}$ alkoxy, halogen, $CF_3$, CN, $N_3$ and $NR_{y1}R_{y2}$ where $R_{y1}$ and $R_{y2}$ are each independently H or $C_{1-4}$ alkyl. Moreover in the case where there are two substituents on adjacent atoms of the ring, e.g.

these substituents P and Q may be linked to form an additional fused ring structure, e.g. a 4-, 5- or 6-membered carbocyclic or heterocyclic ring. This additional ring structure may include for example up to two hetero atoms or groups such as O, S or NH, and it may also be substituted by one or more substituents, e.g. a $C_{1-4}$ alkyl group or groups or a phenyl or substituted phenyl group. In some embodiments, Y may also be adamantyl.

Examples of ring structures represented by Y include where V and W are each selected independently from
O, S, NR' (R' is H or $C_{1-4}$ alkyl)
and $CH_2$ (or —CH—); and
$R_1$ and $R_2$ are each H or $C_{1-4}$ alkyl.

As indicated above, these ring structure can optionally bear substituents which may be the same or different and which may inter alia be selected from H, $C_{1-4}$ alkyl, $C_{1-4}$ alkoxy, —OH, $NR_1R_{y2}$ (where $R_{y1}$ and $R_{y2}$ are each independently H or $C_{1-4}$ alkyl), $CF_3$, halogen, $N_3$, CN, optionally substituted aryl (e.g. phenyl), and optionally substituted aralkyl (e.g. benzyl). Also, as already indicated, it may be useful in some cases for the ring structure to include a plurality of polar substituents such as hydroxyl for example.

In general, the pharmaceutical compositions of this invention will contain an effective CDK-inhibiting non-toxic amount of the active pyrimidine compound, and will be formulated in accordance with any of the methods well known in the art of pharmacy for administration in any convenient manner. The compounds may for example be presented in unit dosage form admixed with at least one other ingredient providing a compatible pharmaceutically acceptable additive, carrier, diluent or excipient.

It will be understood that where reference is made in this specification to compounds of formula I such reference should be construed as extending also to their pharmaceutically acceptable salts and to other pharmaceutically acceptable bioprecursors (pro-drug forms) where relevant. The term "pro-drug" is used in the present specification to denote modified forms or derivatives of a pharmacologically active compound which biodegrade in vivo and become converted into said active compound after administration, especially oral or intravenous administration, in the course of therapeutic treatment of a mammal. Such pro-drugs are commonly chosen because of an enhanced solubility in aqueous media which helps to overcome formulation problems, and also in some cases to give a relatively slow or controlled release of the active agent.

It should also be understood that where any of the compounds referred to can exist in more than one enantiomeric and/or diastereoisomeric form, all such forms, mixtures thereof, and their preparation and uses are within the scope of the invention. It should be noted, however, that stereochemical considerations are likely to be important and there may be considerable selectivity such that different enantiomers or diastereoisomers have significantly different inhibitory activity.

The invention also includes of course the use of the CDK inhibiting compounds referred to for the manufacture of medicaments or pharmaceutical compositions as referred to above, and it also includes the treatment of abnormal cellular proliferation disorders using such medicaments or pharmaceutical compositions. It further includes some pyrimidine compounds which are new chemical entities useful as intermediates in the synthesis of said CDK inhibiting compounds.

Preferably, in compounds in accordance with structural formula I used in carrying out the invention, D will be an unsubstituted amino group —$NH_2$, and X will be oxygen.

Although it will usually be preferred that Y should comprise a saturated or partially saturated carbocyclic or heterocyclic ring structure, it should be recognised that in some cases Y may comprise an aromatic ring system (e.g. optionally substituted aryl or aralkyl), and still provide compounds of interest as potentially selective CDK inhibitors that may be useful in the context of the present invention, especially insofar as they may be structured so as to bind with CDK's in substantially the same manner as depicted in FIG. 2.

Although a number of the CDK inhibitor compounds herein disclosed are already known per se, as previously pointed out some of the compounds are believed to be novel and to constitute new chemical entities.

Examples of compounds which are at present especially preferred for use in carrying out the invention, either directly or as intermediate compounds, and which include the most potent CDK inhibitors that have been identified, at least when assayed in vitro against CDK1 and/or CDK2, include the following:

2,6-Diamino-4-cyclohexylmethoxy-5-nitroso pyrimidine;

2,5,6-Triamino-4-cyclohexylmethyloxypyrimidine;

2,6-Diamino-5-(4'-Chlorophenyl)azo-4-cyclohexyl methoxypyrimidine;

2,6-Diamino-4-benzyloxypyrimidine;

2,6-Diamino-4-benzyloxy-5-nitrosopyrimidine;

2,5,6-Triamino-4-Benzyloxypyrimidine;

2,6-Diamino-4-cyclohex-3-enylmethyloxypyrimidine;

2,6-Diamino-4-cyclohex-3-enylmethyloxy-5-nitroso pyrimidine;

2-Amino-4-cyclohexylmethyloxy-6-methylamino pyrimidine;

2-Amino-6-benzylamino-4-cyclohexylmethyloxy pyrimidine; and 2,6-Diamino-4-cyclohexyl-methyloxypyrimidine-5-carbaldehyde.

Biological Activity

Assays are available for testing the inhibitory activity of the compounds of interest against a range of CDK/cyclin complexes, including CDK1/cyclin A, CDK1/cyclin B, CDK1/cyclin F, CDK2/cyclin A, CDK2/cyclin E, CDK4/cyclin D, CDK5/35 and CDK6/cyclin D3, and it is of particular interest to note the selectivity of some of the compounds against different CDK's.

Test results showing CDK inhibitory activity values measured for some of the compounds that have been prepared are shown in Table 1 at the end of the present description. Where the compounds exist in different enantiomorphic forms, the assays have generally been carried out on racemic mixtures. Apart from reference compounds, the compounds listed are accompanied by an NU reference or identification code number. Table 1 includes the compounds which at present are the most preferred of those that have been prepared, although as yet not all have been fully tested.

In general, the studies carried out fully support the belief that CDK inhibitory characteristics of compounds tested reflect an ability of these compounds to act as effective antitumour drugs.

The inhibition assays have been carried out using methods based on those described in the paper hereinbefore referred to of J. Vesely et al and in the paper of L. Azzi et al (1992) Eur. J. Biochem. 203, 353–360. By way of example, however, a typical protocol is summarised below.

CDK Assay Example

Reagents:

Buffer C (containing 60 mM b-glycerophosphate, 30 mM nitrophenyl phosphate, 25 mM MOPS pH 7.0, 5 mM EGTA, 15 mM MgCl$_2$, 1 mM MgCl$_2$ and 0.1 mM sodium orthovanadate) is made up as follows:

|  | FW | g/100 ml | Final conc |
|---|---|---|---|
| b-glycerophosphate (RT) | 216 | 1.3 | 60 mM |
| MOPS (RT) | 209.3 | 0.52 | 25 mM |
| EGTA (RT) | 380.4 | 0.19 | 5 mM |
| MgCl$_2$ (RT) | 203.4 | 0.305 | 15 mM |

First dissolve above ingredients in about 80 ml distilled water and pH to 7.0

Then add 1 ml 10 mM sodium orthovanadate
   (1.84 mg/ml–FW=183.9 RT)
   final conc=0.1 mM cool to 4° C.

Then Add

| | | | |
|---|---|---|---|
| 4-nitrophenyl phosphate (–20° C.) | 279.2 | 1.112 | 30 mM |
| DTT (4° C.) | 154.2 | .0154 | 1 mM |

(Alternatively, make up 100 mM DTT (15.4 mg/ml) and store in 1.2 ml aliquots in freezer, thaw and add 1 ml to buffer, above)

Make up to 100 ml and store in 5 ml aliquots in freezer Affinity purified p34 cdc2(CDK1)/cyclinB from M-phase starfish (*Marchasterias glacialis*) in 20% glycerol is stored at –80° C. in chest freezer 100 mM Olomoucine (Cat #LC-0-3590-M025 Alexis Co. Bingham Nottinghamn). FW=298.35 29.835 mg/ml= 10 mM, 25 ml aliquots stored in freezer.

1% phosphoric acid (58.8 ml 85% phosphoric acid+4.942 liters water)

Make up the Following on Day of Assay:

Histone H1 (type III-S (Sigma) 4° C.) 5 mg/ml in buffer C. [$^{32}$P]ATP 75 mM: Make up using (multiples of) the following proportions:

2 ml [$^{32}$P]ATP (300Ci/mMol PB168 Amersham, stored in radioactive freezer)+7.5 ml 1 mM cold ATP (–20° C.) (0.551 mg/ml–200 ml aliquots stored in freezer)+90.5 ml buffer C Conc.=12.5 mM in final assay

Assay Procedure

DMSO cannot exceed 1% in the assay mixture. Inhibitors are added at $^{1}\!/_{10}$ final assay volume and 10× final strength. DMSO stocks must therefore be diluted to 10× final desired concentration in ≦10% DMSO, ≧90% buffer C. Suggested concentration ranges=0, 1, 10, 100 mM so DMSO stocks of 0, 100, 1,000 and 10,000 mM are diluted $^{1}\!/_{10}$ in buffer C before adding to assay.

Preparation:

Label set of 0.2 ml microtubes for assay (e.g. A$_0$, A$_1$, A$_{10}$, A$_{100}$) in suitable rack and another set of eppendorfs for drug dilution Label phosphocellulose filters in pencil (e.g. A$_0$, A$_1$, A$_{10}$, A$_{100}$) and fold longitudinally to make a "pitched roof"

Set up water bath at 30° C. containing second rack for microtubes

Set up beaker containing wire mesh insert and magnetic flea below mesh insert, together with 400 ml 1% phosphoric acid, on magnetic stirrer Reaction Mix:

All reagents (except DMSO stocks) should be kept on ice until assay initiated.

Place rack of assay tubes on ice

In each tube put:
   16 ml buffer C
   1 ml cdc2/cyclinB kinase
   5 ml histone H1
   3 ml inhibitor Start reaction in each tube at 30 second intervals by adding
    5 ml [$^{32}$P]ATP vortexing and placing in rack in water-bath at 30° C.
Terminate reaction after 10 min at 30 second intervals in tubes in same order by removing
    25 ml reaction mix and spotting onto appropriately labelled filter, allowing to dry for 20–30 seconds and transferring to stirring 1% phosphoric acid.
Blank incubation is performed as above but without histone (add 5 ml buffer C instead) Washing blank is 5 ml ATP added directly to filter.
Wash filters 5–6 times 5 min each
Dry the filters on paper towel
Count in mini scintillation vials with 5 ml scintillant.
3×standards of 5m1 ATP counted also (375 pmoles ATP)
NB. The assay can be simplified by making up stock reaction mix as follows:
    (1 part cdc2/cyclinB, 16 parts buffer C, 5 parts histone H1)×Number of assay tubes +1 and add 22 ml to each assay tube containing 3 ml buffer C±inhibitor. It is still necessary, however, to make up assay blank (i.e. without histone) separately.

DESCRIPTION OF ILLUSTRATIVE EXAMPLES

The following examples and description of stages in synthetic routes of preparation of various exemplary compounds of interest serve further to illustrate the present invention, but should not be construed in any way as a limitation thereof. Again, in many instances the compounds described are accompanied by an NU reference or identification code number.

2,6-Diamino-4-cyclohexylethoxypyrimidine (NT6034) (for Use as an Intexmediate Compound)

Cyclohexylmethanol (30 ml) and sodium (0.76 g, 32 mmol) were heated together under $N_2$ at 150° C. for 1.5 h. 4-Chloro-2,6-diaminopyrimidine (4.32 g, 30 mmol) was added and the reaction mixture was heated under reflux for 2 h at 180° C. under $N_2$. The solvent was removed under vacuum at the oil pump using a short path distillation apparatus. The resulting residue was purified by column chromatography, using 10% methanol in dichloromethane as the eluent. The final product was further purified by recrystallisation from methanol (4.69 g, 70%), m.p. 142° C.; (Found: C, 59.35; H, 8.21; N, 25.17% $C_{11}H_{18}N_4O$ requires C, 59.45; H, 8.11; N, 25.23%); $\delta_H$ (200 MHz, $d_6$-DMSO) 1.03–1.37 (5H, m, $C_6H_{11}$), 1.79–1.84 (6H, m, $C_6H11$), 4.00 (2H, d, $OCH_2$, J=6.3 Hz), 5.13 (1H, s, C(5)H), 5.96 (2H, br s, $NH_2$), 6.10 (2H, br s, $NH_2$); m/z (+EI) 222 ($M^+$, 29%), 139 ($M^+$-$C_6H_{11}$, 42), 126 ($MH^+$-$C_7H_{13}$, 100), 110 ($MH^+$-$C_7H_{13}O$, 28), 98 (82).

2,6-Diamino-4-cyclohexylmethoxy-5-nitrosopyrimidine (NU6027)

2,6-Diamino-4-cyclohexylmethoxypyrimidine (0.28 g, 1.26 mmol) was dissolved in warm glacial acetic acid solution (30%, 10 ml). The solution was heated to 80° C. and sodium nitrite solution (0.12 g, 1.72 mmol in 5 ml of $H_2O$) was added dropwise over 1 h, until and excess of oxidant, as indicated by starch iodide paper, was observed. The reaction mixture was allowed to cool to room temperature and the violet crystals were collected by filtration, and washed well with water. The title compound was purified by recrystallisation from ethanol (0.26 g, 83%), m.p. 254° C.; (Found: C, 52.73; H, 6.59; N, 27.56% $C_{11}H_{17}N_5O_2$ requires C, 52.59; H, 6.77; N, 27.89%); $\delta_H$ (200 MHz, $d_6$-DMSO) 1.09–1.38 (5H, m, $C_6H_{11}$), 1.73–2.00 (6H, 5 m, $C_6H_{11}$), 4.39 (2H, d, $OCH_2$, J=6.3 Hz), 7.86 (2H, br s, $NH_2$), 8.08 (1H, br s, NH), 10.19 (1H, br s, NH); m/z (+EI) 251 ($M^+$, 25%), 155 ($M^+$-$C_7H_{13}$, 100), 138 ($M^+$-$C_7H_{13}O$, 72), 81 (9).

2,5,6-Triamino-4-cyclohexylmethyloxypyrimidine (NU6035)

To a strirred suspension of 2,6-diamino-5-nitroso-4-cyclohexylmethoxypyrimidine (0.10 g, 0.4 mmol) in water (5 ml) at 50° C. was added sodium dithionite (0.16 g, 0.92 mmol) in portions over a period of 5 h. The reaction mixture was allowed to cool to room temperature and stirred at ambient temperature overnight. The pH of the solution was adjusted to 7 with aqueous ammonia solution (2 ml), and the resulting fine yellow precipitate was collected by filtration and washed with water. The product was purified by recrystallisation from water (0.06 9, 60%), m.p. 154° C.; (Found: C, 55.50; H, 7.95; N, 29.34% $C_{11}H_{19}N_5O$ requires C, 55.69; H, 8.02; N, 29.53%); $\delta_H$ (200 MHz, $d_6$-DMSO) 1.02–1.39 (5H, m, $C_6H_{11}$), 1.71–1.89 (6H, m, $C_6H_{11}$), 3.22 (2H, br s, $NH_2$), 4.03 (2H, d, $OCH_2$, J=6.53 Hz), 5.32 (2H, br s, $NH_2$), 5.71 (2H, br s, $NH_2$); m/z (+EI) 237 ($M^+$, 84%), 155 ($MH^+$-$C_7H_{13}$, 100), 124 ($MH^+$-$C_7H_{13}O$, 15).

4-Chlorobenzenediazonium Tetrafluoroborate (for Use as an Intermediate Compound)

4-Chloroaniline (1.0 g, 7.87 mmol) was suspended in 6 M HCl (4 ml), and the stirred reaction mixture was cooled to 0° C. A solution of sodium nitrite (0.54 g, 7.87 mmol) in water (1 ml) was added dropwise over 5 minutes, and the mixture was stirred at 0° C. for a further 20 minutes. Ice cold fluoroboric acid (40%, 1.14 ml, 18.11 mmol) was added in a single portion, and the mixture was allowed to warm to room temperature over 12 h. After cooling in an ice bath, the resulting precipitate was collected by filtration, and washed sequentially with water, methanol and diethyl ether. The compound was purified by precipitation from cold acetone; $\delta_H$ (200 MHz, $d_6$-DMSO) 8.24 (2H, dd), 8.810 (2H, dd).

2,6-Diamno-5-(4'-Chlorophenyl)azo-4-cyclohexylmethoxypyrimidine (NU6037)

To a stirred solution of 4-chlorobenzenediazonium tetrafluoroborate (0.09 g, 0.68 mmol) in dry DMF (5 ml) under $N_2$ at 0° C., was added 2,6-diamino-4-cyclohexylmethoxypyrimidine (0.15 g, 0.68 mmol), and the stirred reaction mixture was allowed to warm to ambient temperature over 72 h. The solvent was removed under reduced pressure, and the residue was triturated with water, and filtered. The desired product was obtained after recrystallisation from methanol (0.094 g, 39%); $\delta_H$ (200 MHz, $d_6$-DMSO) 1.14–1.47 (5H, m, $C_6H_{11}$), 1.81–1.95 (6H, m, $C_6H_{11}$), 4.31 (2H, d, $OCH_2$, J=6.04 Hz), 7.36 (2H, br s, $NH_2$), 7.62 (2H, d, Ar C(3)Hand Ar (C)5, J=8.7 Hz), 7.85 (2H, d, Ar C(2)H and Ar C(6)H J=8.72 Hz), 8.04 (1H, br s, NH).

2,6-Diamino-4-benzyloxypyrimidine (NU6038)

Sodium (0.41 g, 17.8 mmol) was added to benzyl alcohol (15 ml) under a nitrogen atmosphere and the mixture was heated at 150° C. for 1.5 h. 2,6-Diamino-4-chloropyrimidine (2.16 g, 14.94 mmol) was added and the reaction mixture was stired at 180° C. for a further 2 h. Volatiles were removed in vacuo and the resulting residue was chromatographed on silia with dichloromethane: methanol (9:1) as eluent, to yield the title product as a white solid (1.98 g, 62%); $v_{max}$/cm$^{-1}$ 3347 (NH), 1498 ($C_6H_5$), 1608 ($C_6H_5$); $\delta_H$ (200 MHz, $d_6$-DMSO) 5.20 (1H, s, C(5)H), 5.32 (2H, s, OCH$_2$), 6.05 (2H, br s, NH$_2$), 6.17 (2H, br s, NH$_2$), 7.41–7.48 (5H, m, C$_6$H$_5$); m/z (+EI) 216 (M$^+$, 100%), 139 (M$^+$-C$_6$H$_5$, 33), 91 (94).

2,6-Diamino-4-benzyloxy-5-nitrosopyrimidine (NU6039)

2,6-Diamino-4-benzyloxypyrimidine (0.5 g, 2.3 mmol) was dissolved in warm acetic acid (30%, 10 ml) and the reaction mixture was heated to 80° C. A solution of sodium nitrite (0.22 g, 3.19 mmol) in water (5 ml) was added dropwise over 1 h, when an excess of oxidant was evident by starch-iodide paper. The reaction mixture was allowed to cool to room temperature, and the violet crystals which deposited were collected and washed with water (0.53 g, 98%), m.p. decomposed 209° C.; (Found: C, 55.32; H, 5.28; N, 26.47% C$_{11}$H$_{11}$N$_5$O$_2$ 0.1 H$_2$O C, 55.98; H, 4.75; N, 29.69%); $\nu_{max}$/cm$^{-1}$ 3408 (NH), 2952 (CH$_2$), 1610 (C$_6$H$_5$), 1518 (NO); $\delta_H$ (200 MHz, d$_6$-DMSO) 5.69 (2H, s, OCH$_2$), 7.44–7.68 (5H, m, C$_6$H$_5$), 8.0 (2H, d, NH$_2$), 8.17 (1H, s, NH), 10.19 (1H, s, NH); m/z (+EI) 245 (M$_+$, 25%), 91 (100), 65 (9).

2,5,6-Triamino-4-Benzyloxypyrimidine (NU6040)

To a suspension of 2,6-diamino-4-benzyloxy-5-nitrosopyrimidine (0.3 g, 1.28 mmol) in water (10 ml) at 50° C. was added sodium dithionite (0.48 g, 2.76 mmol) in portions over 5 h. The reaction mixture was stirred at room temperature overnight, heated again to 50° C. and a further quantity of sodium dithionite (0.4 g) was added. After stirring for a further 12 h, the reaction mixture was cooled to room temperature, and the solution was adjusted to pH 7 with aqueous ammonia solution (0.2 ml). The resultant fine yellow solid which deposited was collected, washed with water and recrystallised from hot water (0.11 g, 35%), m.p. 130–135° C.; $\nu_{max}$/cm$^{-1}$ 3394 (NH$_2$), 3033 (C$_6$H$_5$); $\delta_H$ (200 MHz, d$_6$-DMSO) 5.36 (2H, s, OCH$_2$), 5.40 (2H, s, NH$_2$), 5.81 (2H, s, NH$_2$), 7.39–7.56 (5H, m, C$_6$H$_5$).

2,6-Diamino-4-cyclohex-3-enylmethyloxypyridine (NU6046)

To a stirred solution of sodium (0.4 g, 17.4 mmol) in 1,2,3,6-Tetrahydrobenzyl alcohol (20 ml, 0.17 mol) under nitrogen at 120° C., was added 2,6-diamino-4-chloropyrimidine (2 g, 13.84 mmol) and the reaction mixture was stirred for a further 2 h at 180° C. The solvents were removed in vacuo and the crude product was purified by chromatography on silica, employing dichloromethane:methanol (9:1) as eluent. Recrystallisation from ethyl acetate-petrol gave the 5 title compound as a yellow solid (1.3 g, 43%), m.p. 89° C.; $\delta_H$ (200 MHz, d$_6$-DMSO) 1.26–2.24 (7H, m, C$_6$H$_7$), 4.16 (2H, d, OCH$_2$, J=6.56 Hz), 5.14 (1H, s, C(5)H), 5.76 (2H, s, C$_2$H$_2$), 5.96 (2H, br s, NH$_2$), 6.10 (2H, br s, NH$_2$); m/z (+EI) 220 (M$^+$, 27%), 125 (MH$^+$-C$_7$H$_{11}$, 97), 98 (25).

2,6-Diamino-4-cyclohex-3-enylmethyloxy-5-nitrosopyrimidine (NU6045)

A solution of 2,6-diamino-4-cyclohex-3-enylmethyloxypyrimidine (0.5 g, 2.27 mmol) in 30% acetic acid solution was heated to 80° C., and sodium nitrite solution (0.22 g, 3.19 mmol, in 10 ml H$_2$O) was added dropwise over 1 h until excess oxidant was in evidence (starch-iodide paper). The reaction mixture was cooled to room temperature and the resultant violet crystals were collected, washed thoroughly with water and dried (0.52 g, 92%), m.p. 237° C.; $\delta_H$ (200 MHz, d$_6$-DMSO) 1.51–2.19 (7H, m, C$_6$H$_7$), 4.51 (2H, d, OCH$_2$, J=5.66 Hz), 5.82 (2H, br s, C$_2$H$_2$), 7.95 (2H, br s, NH$_2$), 8.15 (1H, br s, NH), 10.21 (1H, br s, NH); m/z (+EI) 249 (M$^+$, 22%), 155 (M$^+$-C$_7$H$_{11}$, 60), 138 (M$^+$-C$_7$H$_{11}$O, 100), 69 (24).

2-Amino-4-chloro-6-methylayninopyrimidine (NU6042) (for Use as an Intermediate Compound)

A mixture of 2-amino-4,6-dichloropyrimidine (1 g, 6.1 mmol), methylamine (0.8 ml), potassium carbonate (0.5 g, 3.62 mmol) and anhydrous ethanol (15 ml) were heated under reflux, under nitrogen, for 18 h. The reaction mixture was cooled to room temperature, filtered, and the filtrate was concentrated to a volume of approximately 2 ml, when a cream solid was obtained (0.82 g, 85%), m.p. 152–157° C.; $\nu_{max}$/cm$^{-1}$ 3442 (NH), 2934 (CH$_3$), 2549 (NH$_2$); $\delta_H$ (200 MHz, d$_6$-DMSO) 3.48 (3H, s, CH$_3$), 5.84 (1H, s, C(5)H), 6.53 (2H, br s, NH$_2$), 7.28 (1H, br s, NH); m/z (+EI) 158 (M$^+$, 100%) , 123 (M$_+$-Cl, 9), 94 (18).

2-Amino-4-cyclohexylmethyloxy-6-methylaminopyriridine (NU6041)

2-Amino-4-chloro-6-methylaminopyrimidine (0.5 g, 2.25 mmol) was added to a stirred solution of sodium (0.062 g, 2.69 mmol) in cyclohexylmethanol (10 ml) under N$_2$, and the reaction mixture was heated at 180° C. for 12 h. Solvents were removed in vacuo and the crude product was purified by chromatography on silica, employing dichloromethane:methanol (9:1) as eluent, to give the title compound as a white solid (0.03 g, 6%), m.p. 128–129° C.; $\nu_{max}$/cm$^{-1}$ 3452 (NH), 2851 (NCH$_3$), 1583 (NH$_2$), 1514 (NH); $\delta_H$ (200 MHz, d$_6$-DMSO) 1.04–1.31 (5H, m, C$_6$H$_{11}$), 2.78 (3H, d, NCH$_3$, J=4.67 Hz), 4.02 (2H, d, OCH$_2$), 5.10 (1H, s, C(5)H), 6.00 (2H, br s, NH$_2$), 6.52 (1H, br d, NH, J=4.22 Hz); m/z (+EI) 236 (M$^+$, 37%), 206 (MH$^+$-NHMe, 31), 153 (M$^+$-C$_6$H$_{11}$, 45), 140 (MH$^+$-C$_6$H$_{11}$CH$_2$O, 100).

2-Amino-6-benzylamino-4-chloropyrimidine (for Use as an Intermediate Compound)

A mixture of 2-amino-4,6-dichloropyrimidine (0.5 g, 3.05 mmol), benzylamine (0.35 ml, 3.2 mmol), potassium carbonate (0.25 g, 1.81 mmol) and ethanol (15 ml) were heated to reflux for 16 h. The reaction mixture was cooled to room temperature and the solvents were removed under reduced pressure. The residue was triturated with ethyl acetate and the white product was collected by filtration. Concentration of the ethyl acetate filtrate also afforded a second crop of product. The combined solids were dried to give the required pyrimidine (0.36 g, 50%), m.p. 136° C.; $\delta_H$ (200 MHz, d$_6$-DMSO) 4.55 (2H, br s, OCH$_2$), 5.87 (1H, br s, C(5)H), 6.54 (2H, br s, NH$_2$), 7.35–7.41 (5H, m, C$_6$H$_5$), 7.72 (1H, m, NH); m/z (+EI) 234 (M$^+$, 85%), 106 (100), 91 (C$_6$H$_5$CH$_2^+$, 51%).

2-Amino-6-benzylamino-4-cyclohexylmethyloxypyrimidine

To a stirred solution of sodium (0.025 g, 1.09 mmol) in cyclohexylmethanol (5 ml, 43 mmol) under nitrogen at 100° C., was added 2-amino-6-benzylamino-4-chloropyrimidine (0.2 g, 0.86 mmol), and the mixture was stirred at 180° C. for 2 h. After removal of solvents, the residue was redissolved in methanol, filtered and the filtrate was evaporated to dryness. The crude product was purified by chromatography on silica, employing petrol: ethyl acetate (8:2) as eluent, to give the title product as a yellow solid (0.13 g, 49%); $\delta_H$ (200 MHz, d$_6$-DMSO) 0.96–1.15 (5H, m, C$_6$H$_{11}$), 1.23–1.34 (6H, m, C$_6$H$_{11}$), 4.03 (2H, br s, OCH$_2$), 4.51 (2H, d, C$_6$H$_5$CH$_2$, J=5.31 Hz), 5.12 (1H, s, C(5)H), 6.56 (2H, br s, NH$_2$), 7.20 (1H, br s, NH), 7.28–7.39 (5H, m, C$_6$H$_5$); m/z (+EI) 312 (M$^+$, 100%), 229 (M$^+$-C$_6$H$_{11}$, 45), 216 (MH$^+$-C$_6$H$_{11}$CH$_2$, 53), 91 (72).

In general, there are a number of routes available for synthesising pyrimidine derivative in accordance with the invention which have a CDK inhibiting activity or which provide intermediates for preparing such CDK inhibiting compounds. By way of example some of the synthetic schemes that may be used, leading in some cases to new chemical entities, are illustrated in the following description of experimental details of typical stages of various synthetic schemes shown in schematic diagrams presented at the end of this description.

Scheme 1

This illustrates the synthesis of 2-amino-4-cyclohexylmethoxy-6-di(4-methoxybenzyl) amino-5-pyrimidine carbaldehyde (NU6057) and the removal therefrom of either one or both benzylamino groups to give 2-amino-4-cyclohexylmethoxy-6-(4-methoxybenzyl) amino-5-pyrimidine carbaldehyde (NU6056) or 2,6-diamino-4-cyclohexylmethoxy-5-pyrimidine carbaldehyde (NU6055) respectively.

1.1 Preparation of 2-Amino-4,6-dichloro-5-pyrimidine Carbaldehyde

Phosphorus oxychloride (21.6 ml; 0.236 mol) was cooled in an ice-bath (~5° C.) before slow addition of dry N,N-dimethylformamide (DMF, 7.0 ml) over 15 mins. No precipitate occurred as previously reported, and the reaction mixture was removed from the ice-bath. Commercially available 2-Amino-4,6-dihydroxypyrimidine (5.6 g; 0.044 mol) was added in small portions over 30 mins. The resulting suspension was heated at 90° C. for 1 h, then at 105° C. for a further 5 h. forming a red-brown solution which was chilled at 4° C. overnight. Distillation of 3–4 ml of excess phosphorus oxychloride at atmospheric pressure produced a viscous suspension which was poured into ice-water (100 ml). A gum formed which dissolved as the temperature of the water increased to 20° C. Ammonium hydroxide was added dropwise until the solution reached pH 7 and a yellow precipitate formed which was collected by filtration. The product was recrystallized from ethyl acetate (5.15 g; 0.027 mol; 61%).

1.2 Preparation of Di-(4-methoxybenzyl)amine

To a solution of 4-methoxybenzaldehyde (3.0 g; 22 mmol) in dry ethanol (40 ml) was added 4-methoxybenzylamine (3.02 g; 22 mmol). The mixture was heated to reflux and heating continued for 1.5 h before 25 removal of the solvent under reduced pressure. TLC analysis indicated that product and starting aldehyde co-elute at $R_f$ 0.8 (10% MeOH/DCM). No attempt was made to isolate the intermediate imine, instead the product was dissolved in methanol (10 ml), to which sodium borohydride (0.834 g; 22 mmol) was added slowly with stirring. The reaction mixture was observed to reflux without additional heat, and was stirred for 1 h. Removal of the solvent yielded a pale yellow oil, which was further purified by column chromatography (100% EtOAc) affording a colourless oil which solidified on cooling to a white solid (5.31 g; 20.7 mmol; 94%).

1.3 Preparation of 2-Amino-4-chloro-6-di-(4-methoxybenzyl)amino-5-pyrimidine Carbaldehyde 2-Amino-4,6-dichloro-5-pyrimidine carbaldehyde (0.50 g; 2.60 mmol) was stirred in dry DCM (5 ml). Triethylamine (0.263 g; 2.60 mmol) and di(4-methoxybenzyl)amine (0.669 g; 2.60 mmol) were added and the reaction stirred at r.t for 1.25 h. the reaction was worked up by addition of further DCM (50 ml) and extraction with saturated sodium chloride solution (3×50 ml). The organic layer was washed with water (50 ml), dried (MgSO$_4$) and evaporated yielding a yellow foam (0.957 g; 2.32 mmol; 89.2%).

In the next stage (1.4) the chloro substituent at position 4 of the pyrimidine ring is replaced by a cyclohexylmethoxy group. Two alternative methods (Method I and Method II) are described.

1.4 Preparation of 2-Amino-4-cyclohexylmethoxy-6-di(4-methoxybenzyl)amino-5-pyrimidine Carbaldehyde (NU6057)

(Method 1)

Cyclohexylmethanol (8 ml) was heated with sodium (0.14 g; 6.06 mmol) at 90° C. for 1 h. 2-Amino-4-chloro-6-di(4-methoxybenzyl)amino-5-pyrimidine carbaldehyde (0.50 g; 1.212 mmol) was added and the mixture heated at the same temperature for 25 mins. Excess cyclohexylmethanol was removed by short path distillation under reduced pressure, and the residue loaded onto MgSO$_4$. The dried product-MgSO$_4$n was applied to a silica column, eluting with 40% EtOAc/ petrol (40:60). Product eluted along with some cyclohexylmethanol, which could not be separated. This mixture was taken through to the next stage.

(Method 2)

Sodium hydride (3 eq; 0.087 g; 3.6 mmol), dry dimethyl sulphoxide (3 ml) and cyclohexylmethanol (5.5. eq; 0.691 g; 6.1 mmol) were stirred under nitrogen for 30 mins until a clear solution had formed. 2-Amino-4-chloro-6-di(4-methoxybenzyl)-amino-5-pyrimidine carbaldehyde (0.50 g; 1.21 mmol) was added with stirring. Reaction mixture was heated at 100° C. for 2 h before removal of the solvent by short path distillation under vacuum. The residue was applied to a silica column eluting with 30% EtOAc/petrol. Product was isolated as a pale yellow solid (0.183 g; 0.37 mmol; 30.6%). M.p. 140–141° C.

Subsequently, either one or both of the benzylamino groups (acting as protective groups) are removed as described below (1.5 and 1.6) to form NU6056 or NU6055.

1.5 Preparation of 2-Amino-4-cyclohexylmethoxy-6-(4-methoxybenzyl)amino-5-pyrimidine Carbaldehyde (NU6056)

The mixture of 2-Amino-4-cyclohexylmethoxy-6-di(4-methoxybenzyl)amino-5-pyrimidine carbaldehyde and cyclohexylmethanol obtained previously was stirred in trifluoroacetic acid (2 ml) for 18 h. Excess trifluoroacetic acid was removed, and the residue extracted with ethyl acetate and water (50 ml each) Further ethyl acetate was added to the aqueous layer, and the organic components combined, dried and evaporated. The residual brown oil was applied to a silica column, eluting with 20% EtOAc/petrol (40:60). A pale yellow oil was obtained. Addition and removal of acetonitrile gave a solid which was recrystallised from a petrol/ethyl acetate mixture (0.091 g; 0.34 mmol) M.p. 97° C.

1.6 Preparation of 2,6-Diamino-4-cyclohexylmethoxy-5-pyrimidine carbaldehyde (NU6055)

The mixture of 2-Amino-4-cyclohexylmethoxy-6-di(4-methoxybenzyl)amino-5-pyrimidine carbaldehyde and cyclohexylmethanol obtained previously was stirred in trifluoracetic acid (2 ml) at 65° C. for 24 h. The same workup procedure was used as previously, with purification of the product by column chromatography eluting with 40% EtOAc/petrol (40:60) yielding a pale yellow solid. M.p. 159–160° C.

Scheme 2

This illustrates a slightly different scheme used to synthesis 2-Amino-4-cyclohexylmethoxy-6-dibenzylamino-5-pyrimidine carbaldehyde.

2.1 Preparation of 2-Amino-4-chloro-6-dibenzylamino-5-pyrimidine Carbaldehyde 2-Amino-4,6-dichloro-5-pyrimidine carbaldehyde (0.15 g; 0.78 mmol) prepared as in Scheme 1 was stirred in dry dichloromethane (3 ml) at 0° C. Dibenzylamine (1 eq; 0.78 mmol; 0.154 g) and triethylamine (1 eq; 0.78 mmol; 0.078 g) were added dropwise. The reaction was allowed to reach r.t, and stirred overnight by which time a clear solution had been obtained.

Further dichloromethane (50 ml) was added and the solution washed with saturated sodium chloride solution and water. The organic layer was dried and evaporated leaving a yellow solid (0.253 g; 0.72 mmol; 92.3%). M.p. 138–142° C.

2.2 Preparation of 2-Amino-4-cyclohexylmethoxy-6-dibenzylamino-5-pyrimidine Carbaldehyde Cyclohexylmethanol (10 ml) and sodium (5 eq; 0.163 g) were reacted at 90° C. for 1 h. 2-Amino-4-chloro-6dibenzylamino-5-pyrimidine carbaldehyde (0.5 g; 1.42 mmol) was added and heating continued for 90 mins. Excess alcohol was removed by short path distillation under reduced pressure, and the product purified further by column chromatography. Product was shown to be contaminated with cyclohexylmethanol by visualisation of the alcohol with sulfuric acid spray (2%).

Scheme 3

This illustrates a route for synthesising pyrimidine derivatives having substituted aralkyl or aralkene groups in the 5-position.

3.1 2-Amino-4-chloro-6-dibenzylamino-5-(1-hydroxy-phenethyl)-pyrimidine (Method based on that described in J. Org. Chem. 1958, 23, 1783–1784).

2-Amino-4-chloro-6-dibenzylamino-5-pyrimidine carbaldehyde (0.10 g; 0.28 mmol), prepared as in Scheme 2 was stirred in dry THF (10 ml) at 0° C. Benzylmagnesium chloride (1.0 M; 3 eq; 0.85 mmol; 0.85 ml) was added dropwise giving a yellow colouration which dissipated quickly. The reaction was stirred for 30 mins before addition of saturated ammonium chloride solution (50 ml) and ethyl acetate (50 ml). The aqueous layer was further extracted with ethyl acetate and the organic layers combined, washed with water, dried and evaporated. The product was purified by column chromatography eluting with 40% EtOAc/petrol (40:60) giving a pale yellow oil (0.086 g; 0.19 mmol; 68%).

3.2 Oxidation of 2-Amino-4-chloro-6-dibenzylamino-5-(1-hydroxyethyl)-pyrimidine to Form Corresponding 5-phenethylene derivative Oxalyl chloride (1.1 eq; 0.0.016 g; 0.12 mmol) was added to dry DCM (5 ml) in a 3-necked flask fitted with a dropping funnel under nitrogen. The flask was chilled in a dry ice-acetone bath at −75–80° C. A solution of DMSO (2.2 eq; 0.25 mmol; 0.02 g) in dry DCM was added dropwise over 5 mins and left stirring for 10 mins. A solution of 2-Amino-4-chloro-6-dibenzylamino-5-(1-hydroxyethyl)-pyrimidine (0.05 g; 0.11 mmol) in dry DCM (5 ml) was added dropwise over 5 mins and the reaction left for 15 mins. Triethylamine (5 eq; 0.56 mmol; 0.057 g) was added dropwise over 5 mins and the cooling bath removed. As the reaction warmed to room temperature, water was added (50 ml) and the organic layer separated. The aqueous phase was washed with further DCM (50 ml) and the organics combined, dried and evaporated. The product was loaded onto a silica column, eluting with 30% EtOAc/petrol (40:60). This gave the product as a yellow oil (0.020 g; 0.05 mmol; 45%), with recovery of some starting material (0.01 g).

For both the above products, which are intermediate compounds, the chloro substituent at position 4 of the pyrimidine ring may be replaced by a cyclohexylmethoxy group by the methods described in Scheme 1.

Scheme 4

This illustrates further examples of the synthesis of pyrimidine derivatives having dibenzylamine substituents in the 6 position and hydroxy or keto substituted alkyl, alkene, aralkyl or aralkene groups in the 5-position.

4.1 Preparation of 2-Amino-4-chloro-6-di-(4-methoxybenzyl)amino-5-(1-hydroxy-phenethyl)-pyrimidine (R=Ph)

2-Amino-4-chloro-6-di(4-methoxybenzyl)amino-5-pyrimidine carbaldehyde (0.20 g; 0.48 mmol) was stirred in dry THF (5 ml) at 0 DC. Benzyl magnesium chloride (1.0 M; 3 eq; 1.45 mmol; 1.45 ml) was added dropwise. The mixture was stirred for, 30 mins before addition of saturated ammonium chloride solution (50 ml) and ethyl acetate (50 ml). The aqueous layer was further extracted with ethyl acetate and the organic layers combined, washed with water, dried and evaporated. The product was purified by column chromatography eluting with 40% EtOAc/petrol (40:60) giving a yellow oil (0.151 g; 0.30 mmol; 62.4%).

4.2 Preparation of 2-Amino-4-chloro-6-di-(4-methoxy-benzyl)amino-5-(1-hydroxyethyl)-pyrimidine (R=H)

Procedure as above with 2-Amino-4-chloro-6-di(4-methoxybenzyl)amino-5-pyrimidine carbaldehyde (0.20 g; 0.48 mmol) and 3.0 M methyl magnesium bromide (3 eq; 0.5 ml). Product obtained as a colourless glass (0.159 g; 0.37 mmol; 77%).

4.3 Oxidation of 2-Amino-4-chloro-6-di-(4-methoxy-benzyl)amino-5-(1-hydroxyethyl)-pyrimidine (R=H) to Form Corresponding 5-ethenyl derivative Oxalyl chloride (1.1 eq; 0.039 g; 0.31 mmol) was added to dry DCM (5 ml) in a 3-necked flask fitted with a dropping funnel under nitrogen. The flask was chilled in a dry ice-chloroform bath at −60° C. A solution of DMSO (2.2 eq; 0.62 mmol; 0.048 g) in dry DCM was added dropwise over 5 mins and left stirring for 10 mins. A solution of 2-Amino-4-chloro-6-di-(4-methoxybenzyl)amino-5-(1-hydroxyethyl)-pyrimidine (0.12 g; 0.28 mmol) in dry DCM (5 ml) was added dropwise over 5 mins and the reaction left for 25 mins. Triethylamine (5 eq; 1.4 mmol; 0.141 g) was added dropwise over 5 mins and the cooling bath removed. The reaction was allowed to warm to room temperature over 40 mins before addition of water (50 ml) and separation of the organic layer. The aqueous phase was washed with further DCM (50 ml) and the organics combined, dried and evaporated. The product was loaded onto a silica column, eluting with 40% EtOAc/petrol (40:60). This gave a yellow oil (0.031 g; 0.08 mmol; 24.5%).

Again, the chloro substituent at position 4 of the pyrimidine ring may be replaced by a cyclohexylmethoxy group using the methods described in Scheme 1 to provide CDK inhibiting compounds in accordance with the invention.

Brief Summary

The present invention should be regarded overall as comprising each and every novel feature or combination of features disclosed herein but the main aspects of the inven tion broadly comprise, principally although not exclusively, the following:

(i) Novel compounds of formula (I) as defined herein;
(ii) Compounds of formula (I) with substituents as hereinbefore defined (including pro-drug forms and salts thereof) for therapy or for use in medicine and in the manufacture of medical preparations, useful for example as CDK inhibitors in treatment of cancer or other cell proliferation disorders.
(iii) Processes for the preparation of novel compounds of formula (I) as defined herein, including any novel intermediate compounds produced in carrying out such processes;
(iv) Pharmaceutical compositions or formulations comprising a compound of formula (I) as defined herein together with a pharmaceutically acceptable carrier therein; and
(v) Processes for the preparation of a pharmaceutical formulation as defined in (iv) above, e.g. by methods referred to herein.

Scheme 1

Scheme 2

Scheme 3

Scheme 4

-continued

TABLE 1

| Number | Name | Structure | % inhibition or IC$_{50}$ ($\mu$M) | | |
|---|---|---|---|---|---|
| | | | CDK1 | CDK2 | CDK4 |
| NU6027 | 2,6-diamino-4-cyclohexyl-methyloxy-5-nitroso-pyrimidine<br>C$_{11}$H$_{15}$N$_5$O$_3$<br>MW = 265.27 | | IC$_{50}$ =2.4, 2.8 | IC$_{50}$ = 2.2 | |
| NU6034 | C$_{11}$H$_{18}$N$_4$O<br>MW = 222.29 | | 4 ± 5 at 10 $\mu$M | 7 ± 3 at 10 $\mu$M | |
| NU6035 | C$_{11}$H$_{19}$N$_5$O<br>MW = 237.30 | | 40 ± 4 at 100 $\mu$M | 54 ± 8 at 100 $\mu$M | |
| NU6037 | C$_{17}$H$_{21}$ClN$_6$O<br>MW = 360.84 | | 3 ± 3 at 10 $\mu$M | 6 ± 4 at 10 $\mu$M | |
| NU6038 | C$_{11}$H$_{12}$N$_4$O<br>MW = 216.24 | | Inactive | Inactive | |
| NU6039 | C$_{11}$H$_{11}$N$_5$O$_2$<br>MW = 245.24 | | 54 ± 9 at 100 $\mu$M | 51 ± 2 at 100 $\mu$M | |

TABLE 1-continued

| Number | Name | Structure | % inhibition or IC$_{50}$ ($\mu$M) | | |
|---|---|---|---|---|---|
| | | | CDK1 | CDK2 | CDK4 |
| NU6040 | 4-benzyloxy-2,5,6-triaminopyrimidine C$_{11}$H$_{13}$N$_5$O MW = 231.25 | | Inactive | Inactive | |
| NU6041 | 2-amino-4-cyclohexyl-methoxy-6-N-methylamino-pyrimidine C$_{12}$H$_{20}$N$_4$O MW = 236.31 | | NT | NT | |
| NU6042 | 2-amino-4-chloro-6-N-methylaminopyrimidine C$_5$H$_7$ClN$_4$ MW = 158.59 | | Inactive | Inactive | |
| NU6044 | 2,5,6-triamino-4-cyclohex-3-enylmethyloxypyrimidine C$_{11}$H$_{17}$N$_5$O MW = 235.28 | | NT | NT | |
| NU6045 | 2,6 diamino-4-cyclohex-3-enylmethyloxy-5-nitroso-pyrimidine C$_{11}$H$_{15}$N$_5$O$_2$ MW = 249.27 | | IC$_{50}$ = 4, 5 $\mu$M | IC$_{50}$ = 6, 4 $\mu$M | |
| NU6046 | 2,6-diamino-4-cyclohex-3-enylmethyloxypyrimidine C$_{11}$H$_{16}$N$_4$O MW = 220.27 | | 16 ± 13 at 100 $\mu$M | 8 ± 1 at 100 $\mu$M | |
| NU6055 | 2,6-diamino-4-cyclohexyl-methyloxypyrimidine-5-carbaldehyde C$_{12}$H$_{18}$N$_4$O$_2$ MW = 250.30 | | 34 ± 4 at 10 $\mu$M | | |

TABLE 1-continued

| | | | % inhibition or IC$_{50}$ ($\mu$M) | | |
|---|---|---|---|---|---|
| Number | Name | Structure | CDK1 | CDK2 | CDK4 |
| NU6056 | 2-amino-6-(4'-methoxy-benzyl)amino-4-cyclohexylmethyloxy-pyrimidine-5-carbaldehyde $C_{20}H_{26}N_4O_3$ MW = 370.45 | | NT | NT | |
| NU6057 | 2-amino-6-di-(4'-methoxy-benzyl)amino-4-cyclohexylmethyloxy-pyrimidine-5-carbaldehyde $C_{28}H_{34}N_4O_4$ MW = 490.60 | | NT | NT | |

What is claimed is:

1. A method for the treatment of a tumour or other cell proliferation disorder in a mammal which comprises administering to a mammal in need of such treatment an antitumour or cyclin dependent kinase-inhibiting amount of a pyrimidine compound having the structural formula I (I)

or a pharmaceutically acceptable salt and/or prodrug form thereof wherein x is O, S or $CHR_x$ where $R_x$ is H or $C_{1-4}$ alkyl;

D is H or $NZ_1Z_2$ where $Z_1$ and $Z_2$ are each independently H, $C_{1-4}$ alkyl, $C_{1-4}$ hydroxyalkyl, optionally substituted aryl or optionally-substituted aralkyl;

A is selected from H, $C_{1-4}$ alkyl, $C_{1-4}$ alkoxy, hydroxy, $CH_2(CH_2)_nOH$ (n=1–4), and $NR_{a1}R_{a2}$ where $R_{a1}$ and $R_{a2}$ are each independently H or $C_{1-4}$ alkyl;

Y is an optionally substituted 5- or 6-membered cycloalkane or cycloalkene ring having one or two double bonds;

D' is H or $NZ_3Z_4$ where $Z_3$ and $Z_4$ are each independently H, $C_{1-4}$ alkyl, $C_{1-4}$ hydroxyalkyl, optionally substituted aryl or optionally-substituted aralkyl;

E is selected from H, NO, $NO_2$, N=N—Ar where Ar is an optionally substituted aryl or optionally substituted aralkyl, $NR_{e1}R_{e2}$ or $NR_{e1}NR_2R_{e3}$ ($R_{e1}$, $R_{e2}$ and $R_{e3}$ each being independently H, $C_{1-4}$ alkyl, $C_{1-4}$ hydroxyalkyl, an optionally substituted aryl or an optionally substituted aralkyl), $C(R_e)=U$ ($R_e$ being hydrogen, $C_{1-4}$ alkyl or substituted alkyl, or an unsubstituted or substituted aryl or aralkyl, and U being selected from O, $NR_e'$, $NOR_e'$ and $N—NR_e'R_e''$ where $R_e'$ and $R_e''$ are each independently H, $C_{1-4}$ alkyl or $CONH_2$), T, $CH_2T$, $CHT_2$ and $CT_3$, where T is a halide I; Br; Cl or F.

2. The method of claim 1 wherein the pyrimidine compound is one in which Y is a ring structure bearing one or more polar hydroxyl substituents.

3. The method of claim 1 wherein the pyrimidine compound is one in which D is an unsubstituted amino group and X is oxygen.

4. The method of claim 1 wherein the compound is one wherein each alkyl or alkoxy group has 1–4 carbon atoms.

5. The method of claim 1 wherein the pyrimidine compound is one of the following:

2,6-Diamino-4-cyclohexylmethoxy-5-nitrosopyrimidine;
2,5,6-Triamino-4-cyclohexylmethyloxypyrimidine;
2,6-Diamino-5-(4'-chlorophenyl)azo-4-cyclohexylmethoxypyrimidine;
2,6-Diamino-4-cyclohex-3-enylmethyloxypyrimidine;
2,6-Diamino-4-cyclohex-3-enylmethyloxy-5-nitrosopyrimidine;
2-Amino-4-cyclohexylmethyloxy-6-methylaminopyrimidine;
2-Amino-6-benzylamino-4-cyclohexylmethyloxypyrimidine; and
2,6-Diamino-4-cyclohexyl-methyloxypyrimidine-5-carbaldehyde.

6. A method according to claim 1 wherein the pyrimidine compound has the formula I wherein Y is an optionally substituted 5- or 6-membered cycloalkane ring.

7. A method according to claim 1 wherein the pyrimidine compound has the formula I wherein Y is an optionally substituted 6-membered cycloalkane ring.

8. A method according to claim 7, wherein the compound is 2,6-diamino-4-cyclohexylmethoxy-5-nitrosopyrimidine.

9. A pyrimidine compound having the structural formula (I)

or a pharmaceutically acceptable salt and/or prodrug form thereof wherein

X is O, S or $CHR_x$ where $R_x$ is H or $C_{1-4}$ alkyl;

D is H or $NZ_1Z_2$ where $Z_1$ and $Z_2$ are each independently H, $C_{1-4}$ alkyl, $C_{1-4}$ hydroxyalkyl, optionally substituted aryl or optionally-substituted aralkyl;

A is selected from H, $C_{1-4}$ alkyl, $C_{1-4}$ alkoxy, hydroxy, $CH_2(CH_2)_nOH$ (n=1–4), and $NR_{a1}R_{a2}$ where $R_{a1}$ and $R_{a2}$ are each independently H or $C_{1-4}$ alkyl;

E is selected from H, NO, $NO_2$, N=N—Ar where Ar is an optionally substituted aryl or optionally substituted aralkyl, $NR_{e1}R_{e2}$ or $NR_{e1}NR_{e2}R_{e3}$ ($R_{e1}$, $R_{e2}$ and $R_{e3}$ each being independently H, $C_{1-4}$ alkyl, $C_{1-4}$ hydroxyalkyl, an optionally substituted aryl or an optionally substituted aralkyl), $C(R_e)$=U ($R_e$ being hydrogen, $C_{1-4}$ alkyl or substituted alkyl, or an unsubstituted or substituted aryl or aralkyl, and U being selected from O, $NR_e'$, $NOR_e'$ and N—$NR_e'R_e''$ where $R_e'$ and $R_e''$ are each independently H, $C_{1-4}$ alkyl or $CONH_2$), T, $CH_2T$, $CHT_2$ and $CT_3$, where T is a halide I; Br; Cl or F;

Y is an optionally substituted 5- or 6-membered cycloalkane or cycloalkene ring having one or two double bonds; and D' is H or $NZ_3Z_4$ where $Z_3$ and $Z_4$ are each independently H, $C_{1-4}$ alkyl, $C_{1-4}$ hydroxyalkyl, optionally substituted aryl or optionally-substituted aralkyl.

10. A compound as claimed in claim 9 wherein each alkyl or alkoxy group present has 1–4 carbon atoms.

11. A compound as claimed in claim 9 wherein the ring Y is substituted with one or more polar hydroxyl substituents.

12. A compound as claimed in claim 9 wherein Y is an optionally substituted 5- or 6-membered cycloalkane or cycloalkene ring having one or two double bonds.

13. A compound as claimed in claim 9 in which D is an unsubstituted amino group and X is oxygen.

14. A pyrimidine compound according to claim 9 selected from the group consisting of:

2,6-Diamino-4-cyclohexylmethoxy-5-nitrosopyrimidine;

2,5,6-Triamino-4-cyclohexylmethyloxypyrimidine;

2,6-Diamino-5-(4'-chlorophenyl)azo-4-cyclohexylmethoxypyrimidine;

2,6-Diamino4-cyclohex-3-enylmethyloxypyrimidine;

2,6-Diamino-4-cyclohex-3-enylmethyloxy-5-nitrosopyrimidine;

2-Amino-4-cyclohexylmethyloxy-6-methylaminopyrimidine;

2-Amino-6-benzylamino4-cyclohexylmethyloxypyrimidine; and 2,6-Diamino-4-cyclohexyl-methyloxypyrimidine-5-carbaldehyde.

15. A pharmaceutical composition comprising an effective tumour cell proliferation inhibiting amount of a compound as claimed in claim 9 or 12 in unit dosage form together with a pharmaceutically acceptable carrier.

16. A compound according to claim 9 wherein Y is an optionally substituted 5- or 6-membered cycloalkane ring.

17. A compound according to claim 9 wherein Y is an optionally substituted 6-membered cycloalkane ring.

18. A compound according to claim 17 which is 2,6-diamino-4-cyclohexylmethoxy-5-nitrosopyrimidine.

19. A pharmaceutical composition according to claim 15 wherein the compound is one wherein Y is an optionally substituted 5- or 6-membered cycloalkane.

20. A pharmaceutical composition according to claim 15 wherein the compound is one wherein Y is an optionally substituted 6-membered cycloalkane.

21. A pharmaceutical composition according to claim 19 wherein the compound is 2,6-diamino-4-cyclohexylmethoxy-5-nitrosopyrimidine.

22. A pharmaceutical composition for treatment of tumours or other cell proliferation disorders in mammals, wherein the active therapeutic ingredient in said composition comprises an effective antitumour and CDK-inhibiting amount of a pyrimidine compound having the structural formula I below:

(I)

or a pharmaceutically acceptable salt and/or prodrug form of said pyrimidine compound, wherein:

X is O, S or $CHR_x$ where $R_x$ is H or $C_{1-4}$ alkyl;

D is H or $NZ_1Z_2$ where $Z_1$ and $Z_2$ are each independently H, $C_{1-4}$ alkyl, $C_{1-4}$ hydroxyalkyl, optionally substituted aryl or optionally-substituted aralkyl;

A is selected from H, $C_{1-4}$ alkyl, $C_{1-4}$ alkoxy, hydroxy, $CH_2(CH_2)_nOH$ (n=1-4), and $NR_{a1}R_{a2}$ where $R_{a1}$ and $R_{a2}$ are each independently H or $C_{1-4}$ alkyl;

Y is an optionally substituted 5- or 6-membered cycloalkane or cycloalkene ring having one or two double bonds;

D' is H or $NZ_3Z_4$ where $Z_3$ and $Z_4$ are each independently H, $C_{1-4}$ alkyl, $C_{1-4}$ hydroxyalkyl, optionally substituted aryl or optionally-substituted aralkyl;

E is selected from H, NO, $NO_2$, N=N—Ar where Ar is an optionally substituted aryl or optionally substituted aralkyl, $NR_{e1}R_{e2}$ or $NR_{e1}NR_{e2}R_{e3}$ ($R_{e1}$, $R_{e2}$ and $R_{e3}$ each being independently H, $C_{1-4}$ alkyl, $C_{1-4}$ hydroxyalkyl, an optionally substituted aryl or an optionally substituted aralkyl), $C(R_e)$=U ($R_e$ being hydrogen, $C_{1-4}$ alkyl or substituted alkyl, or an unsubstituted or substituted aryl or aralkyl, and U being selected from O, $NR_e'$, $NOR_e''$ and N—$NR_e'R_e''$ where $R_e'$ and $R_e''$ are each independently H, $C_{1-4}$ alkyl or $CONH_2$), T, $CH_2T$, $CHT_2$ and $CT_3$, where T is a halide I; Br; Cl or F, said active therapeutic ingredient being admixed with at least one other ingredient which provides a compatible pharmaceutically acceptable carrier therefor.

23. A method for inhibiting cyclin dependent kinase activity in a mammal which comprises administering to a mammal in need of such inhibition, an effective amount of a pyrimidine compound having the structural formula I (I)

or a pharmaceutically acceptable salt and/or prodrug form thereof wherein

X is O, S or $CHR_x$ where $R_x$ is H or $C_{1-4}$ alkyl;

D is H or $NZ_1Z_2$ where $Z_1$ and $Z_2$ are each independently H, $C_{1-4}$ alkyl, $C1_4$ hydroxyalkyl, optionally substituted aryl or optionally-substituted aralkyl;

A is selected from H, $C_{1-4}$ alkyl, $C_{1-4}$ alkoxy, hydroxy, $CH_2(CH_2)_nOH$ (n=1–4), and $NR_{a1}R_{a2}$ where $R_{a1}$ and $R_{a2}$ are each independently H or $C_{1-4}$ alkyl;

Y is an optionally substituted 4- to 8-membered carbocyclic ring;

D' is H or $NZ_3Z_4$ where $Z_3$ and $Z_4$ are each independently H, $C_{1-4}$ alkyl, $C_{1-4}$ hydroxyalkyl, optionally substituted aryl or optionally-substituted aralkyl; and E is selected from H, NO, $NO_2$, N=N—Ar where Ar is an optionally substituted aryl or optionally substituted aralkyl, $NR_{e1}R_{e2}$ or $NR_{e1}NR_{e2}R_{e3}$ ($R_{e1}$, $R_{e2}$ and $R_{e3}$ each being independently H, $C_{1-4}$ alkyl, $C_{1-4}$ hydroxyalkyl, an optionally substituted aryl or an optionally substituted aralkyl), $C(R_e)$=U ($R_e$ being hydrogen, $C_{1-4}$ alkyl or substituted alkyl, or an unsubstituted or substituted aryl or aralkyl, and U being selected from O, $NR_e'$, $NOR_e'$ and N—$NR_e'R_e''$ where $R_e'$ and $R_e''$ are each independently H, $C_{1-4}$ alkyl or $CONH_2$), T, $CH_2T$, $CHT_2$ and $CT_3$, where T is a halide I; Br; Cl or F.

24. A method according to claim 23 wherein the pyrimidine compound has the formula I wherein Y is an optionally substituted 5- or 6-membered cycloalkane ring.

25. A method according to claim 23 wherein the pyrimidine compound has the formula I wherein Y is an optionally substituted 6-membered cycloalkane ring.

26. A method according to claim 24 wherein the compound is 2,6-diamino-4-cyclohexylmethoxy-5-nitrosopyrimidine.

27. The method of claim 1 wherein said compound of formula I is the sole antitumour compound administered.

28. The method of claim 27 wherein the pyrimidine compound is one in which Y is an optionally substituted 5- or 6-membered cycloalkane or cycloalkene ring having one or two double bonds.

* * * * *

UNITED STATES PATENT AND TRADEMARK OFFICE
CERTIFICATE OF CORRECTION

PATENT NO. : 6,677,345 B1
DATED : January 13, 2004
INVENTOR(S) : Roger J. Griffin et al.

It is certified that error appears in the above-identified patent and that said Letters Patent is hereby corrected as shown below:

<u>Title page,</u>
Item [30], please insert

-- [30]   Foreign Application Priority Data

9806739.0   (GB) ................................ March 28, 1998 --

Signed and Sealed this

Thirtieth Day of March, 2004

JON W. DUDAS
*Acting Director of the United States Patent and Trademark Office*